(12) United States Patent
Pandey et al.

(10) Patent No.: US 7,872,144 B2
(45) Date of Patent: Jan. 18, 2011

(54) PROCESS FOR PRODUCING BIPHOSPHONIC ACIDS AND FORMS THEREOF

(75) Inventors: Satish Chandra Pandey, Noida (IN); Hussain Haider, Noida (IN); Sudhanshu Saxena, Noida (IN); Manoj Kumar Singh, Noida (IN); Rajesh Kumar Thaper, Noida (IN); Sushil Kumar Dubey, Noida (IN)

(73) Assignee: Jubilant Organosys Limited, Noida (IN)

(*) Notice: Subject to any disclaimer, the term of this patent is extended or adjusted under 35 U.S.C. 154(b) by 502 days.

(21) Appl. No.: 11/922,064

(22) PCT Filed: Jun. 13, 2005

(86) PCT No.: PCT/IN2005/000192

§ 371 (c)(1),
(2), (4) Date: Dec. 11, 2007

(87) PCT Pub. No.: WO2006/134603

PCT Pub. Date: Dec. 21, 2006

(65) Prior Publication Data

US 2009/0312551 A1  Dec. 17, 2009

(51) Int. Cl.
*C07F 9/38* (2006.01)
*C07F 9/06* (2006.01)

(52) U.S. Cl. ............ 548/112; 546/22; 546/23; 564/15

(58) Field of Classification Search .......... None
See application file for complete search history.

(56) References Cited

U.S. PATENT DOCUMENTS

| 4,407,761 A | 10/1983 | Blum et al. |
| 4,922,007 A | 5/1990 | Kieczykowski et al. |
| 5,019,651 A | 5/1991 | Kieczykowski |
| 5,648,491 A | 7/1997 | Dauer et al. |
| 5,908,959 A | 6/1999 | Kubela et al. |
| 6,410,520 B2 | 6/2002 | Cazer et al. |
| 6,562,974 B2 | 5/2003 | Cazer et al. |
| 6,573,401 B1 | 6/2003 | Bosch i Llado et al. |
| 2003/0195170 A1 | 10/2003 | Aronhime et al. |
| 2004/0043967 A1 | 3/2004 | Lidor-Hadas et al. |
| 2005/0054616 A1 | 3/2005 | Aronhime et al. |

*Primary Examiner*—Kamal A Saeed
*Assistant Examiner*—Nyeemah Grazier
(74) *Attorney, Agent, or Firm*—Blank Rome LLP

(57) ABSTRACT

Disclosed herein is a process for producing bisphosphonic acids and salts thereof. The process comprising reacting a carboxylic acid of Formula [I] with phosphorous acid and halophosphorus compound in the presence of a solvent selected from aliphatic hydrocarbon or water miscible cyclic ether. Further, the present invention also provides novel forms of bisphosphonic acids and process for preparation thereof.

12 Claims, 6 Drawing Sheets

PROCESS FOR PRODUCING BIPHOSPHONIC ACIDS AND FORMS THEREOF

CROSS REFERENCE TO RELATED APPLICATIONS

This application is the U.S. national phase of PCT/IN2005/000192 filed Jun. 13, 2005. The PCT application published in English as WO2006/134603 A1.

FIELD OF THE INVENTION

In general, this invention relates to a process for producing bisphosphonic acid and its forms thereof. More particularly, but without limitation to the preferred embodiment of the present invention, there is provided a novel process for producing bisphosphonic acid employing a selective solvent. Further, the present invention also provides novel forms of bisphosphonic acids and processes of preparation thereof.

BACKGROUND OF THE INVENTION

The bisphosphonic acid or its pharmaceutically acceptable salts are important class of medicaments useful in the treatment of diseases of bone and calcium metabolism. Such diseases include osteoporosis, hyperparathyroidism, hypercalcemia of malignancy, ostolytic bone metastases, myosistis ossificans progressiva, calcinoisis universalis, arthritis, neuritis, bursitis, tendonitis and other inflammatory conditions. In particular bisphosphonates, like ethane-1-hydroxy-1,1-diphosphonic acid (EHDF), propane-3-amino-1-hydroxy-1,1-diphosphonic acid (APD), dichloromethane diphosphonic acid, 3-amino-1-hydroxypropylidenediphosphonic acid (PAMIDRONIC ACID), 4-amino-1-hydroxybutylidene-1,1-diphosphonic acid (ALENDRONIC ACID), 1-hydroxy-2-(1-imidazolyl)ethylidine-1,1-diphosphonic acid (ZOLEDRONIC ACID) and 1-hydroxy-2-(3-pyridinyl)ethylidene-1,1-diphosphonic acid (RISEDRONIC ACID) have been the subject of considerable research efforts in this area. Paget's disease and heterotropic ossification are currently successfully treated with EHDP and Risedronic acid. The diphosphonates tend to inhibit the resorption of bone tissue, which is beneficial to patients suffering from excessive bone loss.

Several methods for making bisphosphonic acids or its pharmaceutically acceptable salts have been disclosed. The syntheses are based on reacting a carboxylic acid with a mixture of phosphorous acid and one of the following phosphorus halides: phosphorus trichloride ($PCl_3$), phosphorus oxychloride ($POCl_3$), phosphorus pentachloride ($PCl_5$), phosphorus tribromide ($PBr_3$), phosphorus oxybromide ($POBr_3$) or phosphorus pentabromide ($PBr_5$), then quenching the reaction mixture with water or a non-oxidizing aqueous acid, followed by heating to hydrolyze the phosphorus intermediates to the final product.

U.S. Pat. No. 4,407,761 describes the synthesis of 4-amino-1-hydroxybutylidene-1,1-bisphosphonic acid (alendronic acid) and other bisphosphonic acids. The reaction has been carried out in the presence of diluent, e.g. chlorinated hydrocarbons, especially chlorobenzene, which does not solubilize the reaction components and serves only as a heat carrier. The reaction starts as a two-phase system, in which the melted phase gradually thickens into a non-stirrable mass. This semi solid sticky mass finally turns into a hard, rigid material, thereby coating the walls of the reaction vessel and thus preventing the smooth heat transfer and complicating the product work-up. The overall yield of this process is variable i.e. 45% to 56%. The solvent i.e. chlorobenzene used in the reaction is carcinogenic in nature and thus not recommendable for industrial scale.

U.S. Pat. No. 4,922,007 and U.S. Pat. No. 5,019,651 reveal a solution to the solidification. Methanesulfonic acid (MSA) is used to solubilize the reaction components and keep the reaction mixture stirrable up to completion of the reaction. The optimum temperature of phosphonylation reactions using phosphorus trichloride is 90° C. or high. Although the problems with physical characteristics of the reaction appeared solved, a safety problem surfaced. Methanesulfonic acid reacts with phosphorus trichloride and under adiabatic conditions, i.e. above 85° C., the reaction mixture becomes uncontrollably exothermic, which is accompanied by high pressure and, therefore, is not very safe on large-scale production.

U.S. Pat. No. 5,908,959 employs polyalkylene glycols as reaction solvent for synthesizing bisphosphonates. The use of polyalkylene glycols on industrial scale is not very feasible as they are difficult to recover in pure form for reuse.

U.S. Pat. No. 5,648,491 describes that the phosphonylation reaction is carried out in a continuous stirred tank reactor. According to this invention more favorable surface/volume ratio results in better heat transfer and the smaller volume of the reaction mixture reduces the probability of an unexpected thermal event. The disadvantage of this process is that special and expensive equipment is required. Moreover, this continuous operation results in the formation of different dimers, oligomers and polymers, which are present as impurities in the product.

According to U.S. Pat. No. 6,573,401 the problems mentioned in the prior art are solved by the use of methanesulfonic anhydride as a solvent for producing alendronic acid with the overall yield of the process is 65-77%, but the high cost of the solvent renders the method difficult to apply at an industrial level.

US Patent Application No. 20040043967 A1 describes the preparation of bisphosphonic acids by using the diluents other than halogenated hydrocarbons, but overall yield of the process is 56% to 80%. On the other hand U.S. Pat. No. 6,562,974 describes the preparation of bisphosphonates in an overall yield of 77% by using phosphorous acid as a reactant/solvent in presence of base. The disadvantage of this process is that the reaction mixture becomes very viscous without a solvent.

Thus there remains a need for a safe, economical and efficient industrial process for preparing bisphosphonic acids that is free from above-mentioned drawbacks and achieves high yields in environmental friendly conditions, which can also be further extended for the preparation of new polymorphs.

Apart from above mentioned process patents few polymorphs patents and patent applications are available. For example US Patent Application no. 20050054616 A1 describes the zoledronic acid or its pharmaceutically acceptable salts in crystalline as well as in amorphous form. This patent application also describes the process for their preparation. U.S. Pat. No. 6,410,520 describes the process for the preparation of risedronate sodium polymorphs in heripentahydrate and monohydrate crystalline forms, whereas US Patent Application no. 20030195170 describes different crystalline forms and their process for preparation of risedronate sodium.

The aim of the present invention is to provide a process, which is safe, economical, environmental friendly and feasible at commercial scale as well as high yielding and above all it is free from all above-mentioned disadvantages of prior art. This process is further extended for the preparation of novel forms of bisphosphonic acid.

SUMMARY OF THE INVENTION

In accordance with the principal embodiment of the present invention, there is provided a process for producing bisphosphonic acids or its pharmaceutically acceptable salts, the process comprising reacting a carboxylic acid with phosphorous acid and halophosphorus compound in the presence of a solvent selected from aliphatic hydrocarbon or water miscible cyclic ether.

In accordance with other embodiment of the present invention, there is provided a process for producing bisphosphonic acids or its pharmaceutically acceptable salts, wherein the process comprises reacting a carboxylic acid with phosphorous acid and halophosphorus compound in the presence of a solvent selected from aliphatic hydrocarbon or water miscible cyclic ether at a temperature between about 60° C. to reflux temperature, refluxing the resultant reaction mixture and cooling the same, adding water to the same, hydrolyzing the reaction mixture, optionally adding antisolvent to the reaction mixture and isolating the resultant bisphosphonic acid from the suspension.

In accordance with yet another embodiment of the present invention, there is provided a method of making a bisphosphonic acid or salts thereof comprising the step of combining a carboxylic acid selected from 4-aminobutanoic acid, (3-pyridyl)ethanoic acid, (imidazol-1-yl)ethanoic acid, 3-(N-(n-pentyl)-N-methylamino)propionic acid, (imidazo[1,2-a]pyridine-3-yl)ethanoic acid, 3-aminopropionic acid, 3-(N,N-dimethylamino)propionic acid, 6-aminohexanoic acid and ethanoic acid or its quaternary salt thereof, phosphorous acid and a halophosphorus compound selected from the group consisting of $PCl_3$, $PBr_3$, $PCl_5$, $PBr_5$, $POCl_3$ and $POBr_3$, preferably $PCl_3$ in the presence of solvent that is a aliphatic hydrocarbon having $C_6$-$C_{10}$ atoms such as hexane, cyclohexane, heptane, cycloheptane, octane and cyclooctane or water miscible cyclic ether such as tetrahydrofuran and dioxane.

Further embodiment of the present invention is to provide a novel crystalline polymorphic form J of a bisphosphonic acid and process for preparation thereof, wherein the said bisphosphonic acid is zoledronic acid.

In other embodiment of the present invention, there is provided a process for preparation of the said polymorphic form J of zoledronic acid comprising refluxing the obtained zoledronic acid by the process mentioned above or from any other process, with distilled water at 95° C. to 100° C. until it is dissolved followed by filtration to get clear solution, stirring the resultant solution at 5° C., filtering and drying the resultant to get crystalline polymorphic form J.

Furthermore, in another embodiment of the present invention, there is provided a novel stable amorphous form of bisphosphonic acid salt and process for preparation thereof, wherein said bisphosphonic acid salt is risedronate sodium.

Another embodiment provides a process for preparation of said amorphous form of risedronate sodium comprising treating the obtained risedronic acid by the process mentioned above or from any other process, with sodium base in water, removing water at low temperature and drying the resultant to obtain an amorphous form of risedronate sodium.

In one other embodiment of the present invention is provided a process for preparation of amorphous form of risedronate sodium, wherein the process comprises, dissolving the obtained risedronate sodium in water, stirring the same to make the solution clear, freezing the solution and removing the water by lyophilization and drying the resultant to obtain an amorphous form of risedronate sodium.

BRIEF DESCRIPTION OF DRAWING FIGURES

Further objects of the present invention together with additional features contributing thereto and advantages accruing there from will be apparent from the following description of preferred embodiments of the invention which are shown in the accompanying drawing figures, wherein.

DETAILED DESCRIPTION OF THE INVENTION

Figure 1:
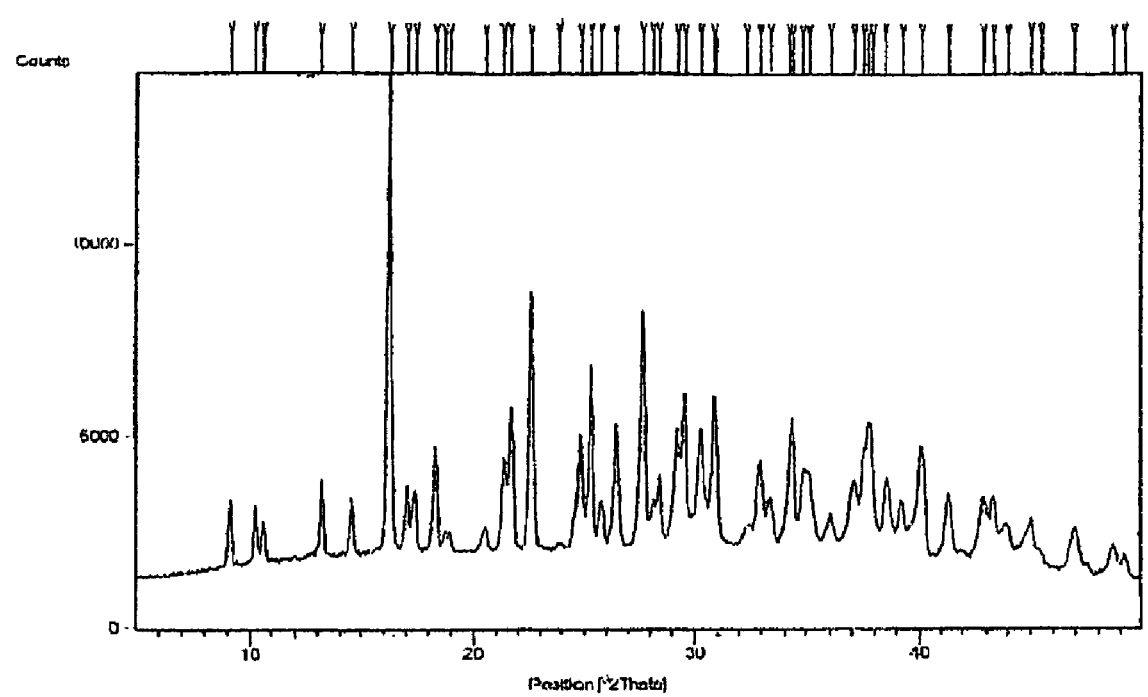
FIG. 1 shows a characteristic X-ray powder diffraction pattern for crystalline form J of zoledronic acid.
Figure 2:
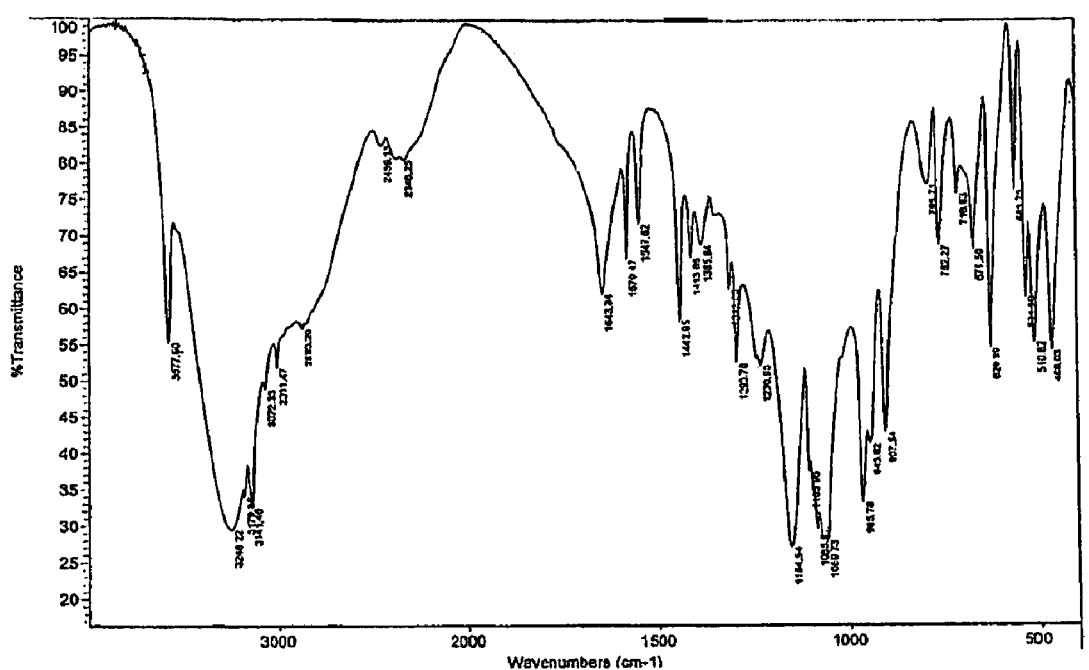
FIG. 2 shows a characteristic infrared absorption spectrum of crystalline form J of zoledronic acid in potassium bromide. [Vertical axis: Transmission (%); horizontal axis: wave number $(cm^{-1})$].
Figure 3:
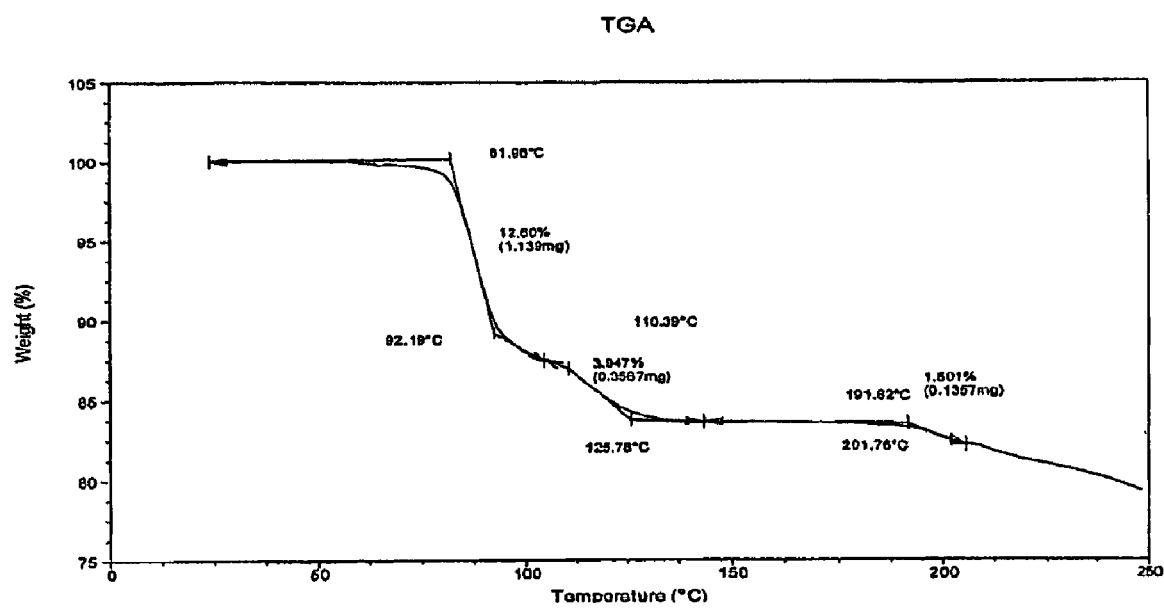
FIG. 3 shows a Thermo gravimetric analysis of crystalline form J of zoledronic acid.

The present invention provides a safe, environmental friendly, economical and commercially feasible process for producing bisphosphonic acids and forms thereof. The process for the preparation of bisphosphonic acid or salt thereof of formula II comprises reacting a carboxylic acid of Formula [I] with phosphorous acid and halophosphorus compound:

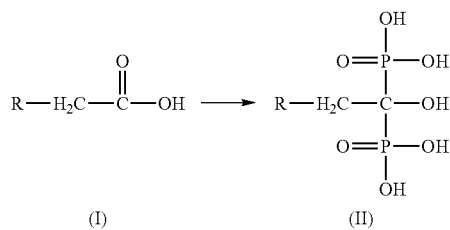

wherein, R is hydrogen, $C_1$-$C_8$ linear or branched alkyl, optionally bearing one or more substituents selected from amino, hydroxy, halo, aryl, heteroaryl, haloaryl, haloheteroaryl; or R is aryl or heteroaryl, optionally substituted with one or more substituents selected from amino, hydroxy, halo, aryl, heteroaryl, haloaryl and haloheteroaryl; or R is either imidazol-1-yl, 3-pyridyl, 2-aminoethyl, (N-(n-pentyl),N-methylamino)methyl, imidazo[1,2-a]pyridin-3-yl, 4-aminobutyl, (N,N-dimethylamino)methyl, hydrogen or aminomethyl.

In particularly preferred embodiments, R is either imidazol-1-yl (i.e. II is zoledronic acid), 3-pyridyl (i.e. II is risedronic acid), 2-aminoethyl (i.e. II is alendronic acid), (N-(n-pentyl),N-methylamino)methyl (i.e. II is ibendronic acid), imidazo[1,2-a]pyridin-3-yl (i.e. II is minodronic acid), 4-aminobutyl (i.e. II is neridronic acid), (N,N-dimethylamino)methyl (i.e. II is olpadronic acid), hydrogen (i.e. II is etidronic acid) or aminomethyl (i.e. II is pamidronic acid).

In the process of the present invention, the compound of formula II is prepared by reacting a carboxylic acid or its quaternary salt thereof (I) with phosphorous acid ($H_3PO_3$) and halophosphorus compound in the presence of a solvent other than halogenated and/or non-halogenated aromatic hydrocarbon.

The solvent used in the present invention is selected from the group consisting of but not limited to aliphatic hydrocarbon having $C_6$-$C_{10}$ atoms selected from n-octane, iso-octane, cyclooctane, n-heptane, cycloheptane, n-hexane and cyclohexane, or water miscible cyclic ethers such as tetrahydrofuran and dioxane, more preferably n-octane, n-heptane, cyclohexane, tetrahydrofuran and dioxane.

The halophosphorus compound used in the process is selected from the group consisting of but not limited to $PCl_3$, $PCl_5$, $POCl_3$, $PBr_3$, PBr5 and $POBr_3$, most preferably $PCl_3$. The amount of halophosphorus compound used is about 2.0 to 6.0 mole equivalents per equivalent of carboxylic acid, most preferably 3.5 to 4.5 mole equivalents. Phosphorous acid used in the process is about 1.0 to 6.0 mole equivalents per equivalent of carboxylic acid, most preferably 3.5 to 4.5 mole equivalents. The solvent used is in an amount of 5 to 40 volumes per weight (volumes per weight is milliliters per gram or liters per kilogram) of carboxylic acid, preferably about 15-25 volumes per weight of the carboxylic acid.

The reaction is carried out at a temperature between about 60° C. to reflux temperature depending on the choice of the solvent used. During the reaction, water is added. The multi phase reaction mixture is heated to a temperature between about 60° C. to reflux for about 4 hrs to 24 hrs, most preferably 15-20 hrs, which dissolves the viscous mass. The amount of water varies from about one fourth to one time the volume, preferably half of the volume of the solvent used. The product bisphosphonic acid is isolated from the aqueous phase optionally by adding water miscible anti-solvent to the reaction mixture. The preferred anti-solvent used is water miscible alcohol, ketone, nitrile and cyclic ether.

The bisphosphonic acids produced by said process comprise zoledronic acid, risedronic acid, alendronic acid, minodronic acid, neridronic acid, pamidronic acid, ibandronic acid, olpadronic acid or etidronic acid and their pharmaceutically acceptable salts.

The process for the preparation of pure zoledronic acid, prepared either from above mentioned process or from any other process known in the literature, further comprises crystallization from water, which yields a new crystalline polymorphic form J of zoledronic acid. This polymorph J of zoledronic acid is characterized by powder X-ray diffraction, FTIR spectroscopy and TGA analysis. The polymorphic form J of zoledronic acid contains about of 16-22% moisture content.

Polymorph J of zoledronic acid is characterized by a powder X-ray diffraction pattern with peaks 16.2, 18.3, 21.3, 21.6, 22.6, 24.8, 25.3, 26.4, 27,6, 29.2, 29.5, 30.2, 30.8, 30.9, 32.9, 34.2, 37.7 and 37.9±0.20 2θ. Polymorph J of zoledronic acid produces a FTIR spectrum with characteristics absorption bands at about 3577, 3248, 1643, 1579, 1442, 1293, 1154, 1085, 1059, 965, 907, 629, 510 and 468 $cm^{-1}$.

Risedronic acid, obtained either from above mentioned process or from any other process known in the literature, is further converted to its sodium salt in water and then this sodium salt of risedronic acid is lyophilized, which leads to a novel amorphous form of risedronate sodium. The process for the preparation of risedronate sodium in amorphous form comprises either the conversion of risedronic acid into its sodium salt by treating risedronic acid with sodium base preferably sodium hydroxide, sodium carbonate, sodium bicarbonate and sodium alkoxide (wherein alkyl contains $C_1$-$C_6$ carbon atoms) in water and then water is removed at low temperature to get solid risedronate sodium which is in amorphous form or by dissolving crystalline form of risedronate sodium in water, followed by freezing and water is subsequently removed by lyophilization, then collecting the solid amorphous form of risedronate sodium as a final product. The amorphous form is characterized by powder X-ray diffraction, FTIR and TGA analysis.

Figure 4:
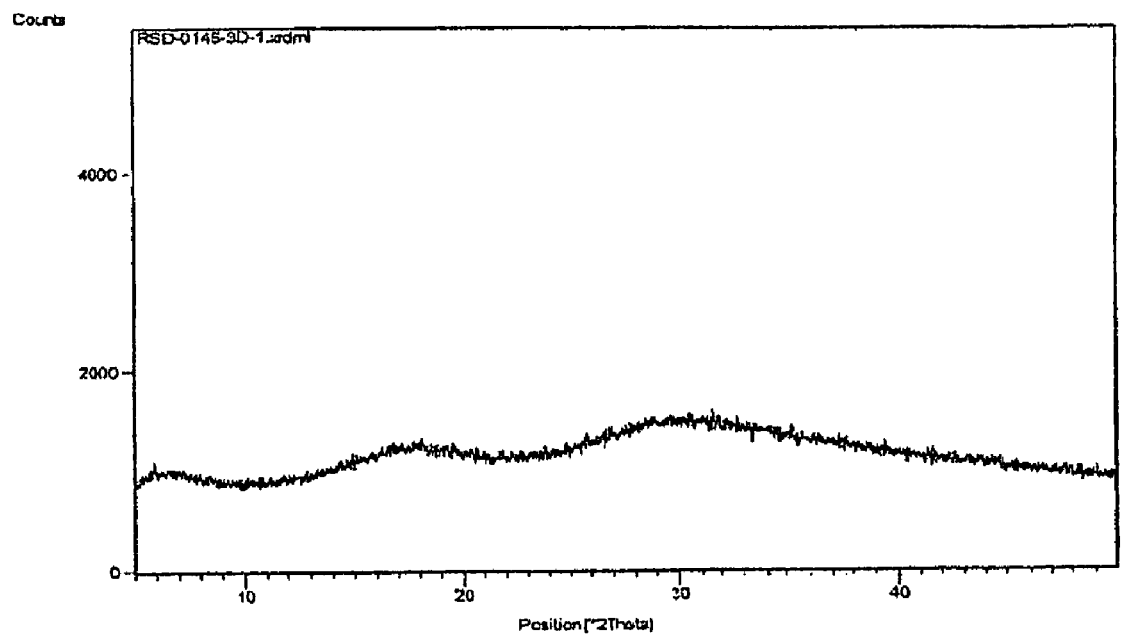
FIG. 4 shows a characteristic X-ray powder diffraction pattern for amorphous risedronate sodium.
Figure 5:
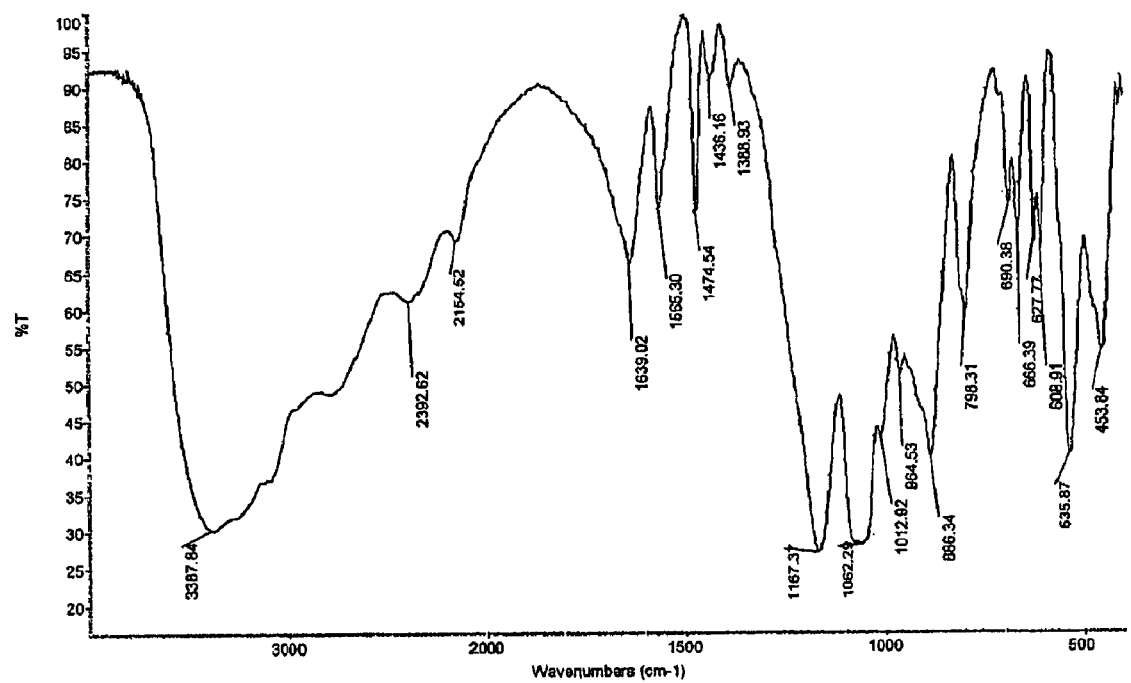
FIG. 5 shows a characteristic infrared absorption spectrum of amorphous risedronate sodium in potassium bromide. [Vertical axis: Transmission (%); horizontal axis: wave number $(cm^{-1})$].
Figure 6:
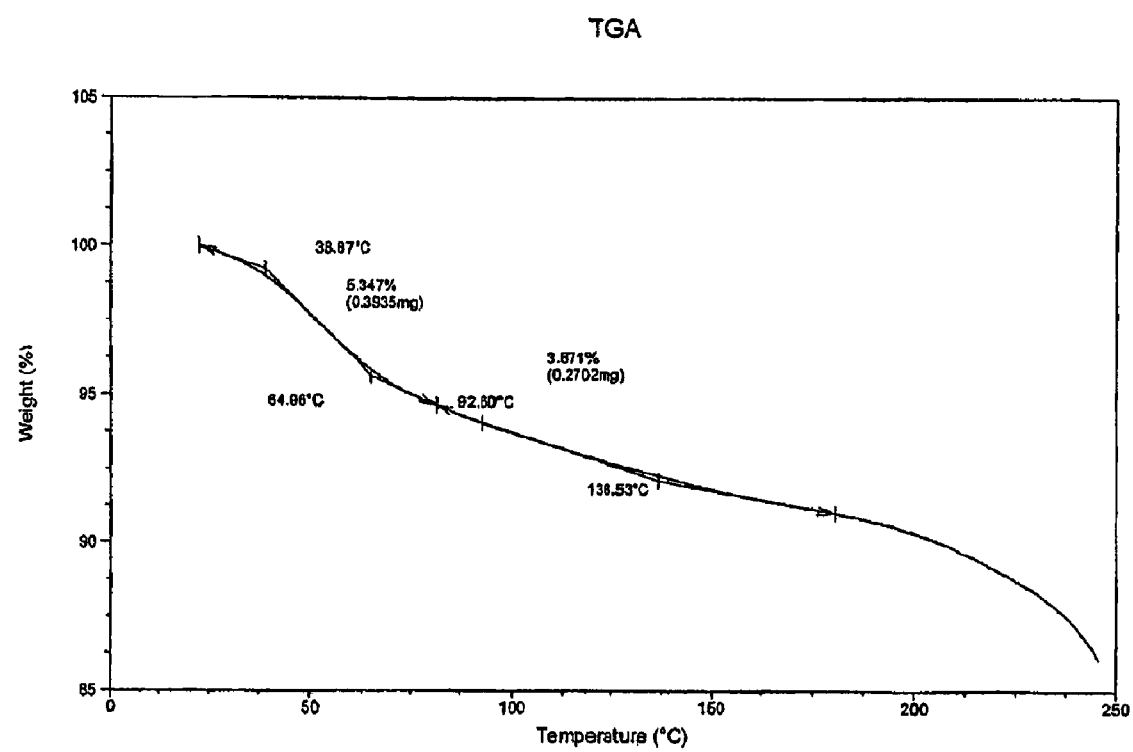
FIG. 6 shows a Thermo gravimetric analysis of amorphous risedronate sodium.

Amorphous form of risedronate sodium is characterized by a powder X-ray diffraction pattern as given in FIG. 4. Amorphous form of risedronate sodium produces a FTIR spectrum with characteristics absorption bands at about 3387, 2392, 2154, 1639, 1565, 1474, 1167, 1062, 886, 798, 666, 535 and 453 $cm^{-1}$. The amorphous risedronate sodium is highly stable and does not degrade at 100° C. for more than 36 hrs. Typically amorphous form has higher bioavailability as compared to its crystalline form. The amorphous risedronate sodium is comparatively more soluble than its crystalline counterpart. The amorphous risedronate sodium is having the moisture content 0.5% to 13.6%.

The advantages of the process for the preparation of bisphosphonic acids or its pharmaceutically acceptable salts over the prior art processes is the continuous mode of work up which reduces the time period for reaction workup as well as increases the feasibility on plant scale. It increases the yield of the final product to 96-98% (as compared to 45-77% mentioned in prior art). The another advantage of this process is the use of non-toxic and environmental friendly conditions for the preparation of bisphosphonic acids in which novel solvent systems are developed, avoiding the halogenated and/or non-halogenated aromatic hydrocarbons as reported in prior art. As compared to halogenated and/or non-halogenated aromatic hydrocarbons, the aliphatic hydrocarbons and cyclic ethers are considered environmentally friendlier, less hazardous and reusable solvents.

In conclusion, this is a novel, improved, safe, environmental friendly, economical, commercially feasible and a high yielding process for the industrial production of bisphosphonic acids or its salt thereof. This process is further extended for the preparation of novel polymorphs of zoledronic acid and risedronate sodium.

The following non-limiting examples illustrate specific embodiments of the present invention. They are, however, not intended to be limiting the scope of present invention in any way.

Example 1

Preparation of Zoledronic Acid
Method—A

Imidazol-1-ylacetic acid (50 gm), phosphorous acid (150 gm) and n-octane (1000 mL) were taken in a four necked round bottom flask fitted with an addition funnel, mechanical stirrer, condenser and thermometer pocket and allowed to stir at 90-95° C. Phosphorus trichloride (250 gm) was then added to the reaction mixture and allowed to heat at 90-95° C. The reaction mixture was cooled and distilled water (500 mL) was added to it. The reaction mixture was further heated to 90-95° C. and then cooled to room temperature, filtered through celite bed. Aqueous layer was separated and methanol (2000 mL) was added to it. The solution was cooled to 0-5° C. and stirred for 4-5 hrs. The precipitated solid was filtered, washed with methanol and dried under vacuum yielding 70 gm of product.

Method—B

Imidazol-1-ylacetic acid (50 gm), phosphorous acid (150 gm) and 1,4-dioxane (1000 mL) were taken in a four necked round bottom flask fitted with an addition funnel, mechanical stirrer, condenser and thermometer pocket and allowed to stir at 90-95° C. Phosphorus trichloride (250 gm) was then added to the reaction mixture and allowed to heat at 90-95° C. The reaction mixture was cooled and distilled water (500 mL) was added to it. The reaction mixture was further heated to 90-95° C. and then cooled to RT and filtered through celite bed. Methanol (2000 mL) was added to the filtrate and cooled to 0-5° C. and stirred for 4-5 hrs. The precipitated solid was filtered, washed with methanol and dried under vacuum to yield 56.0 gm of product.

Preparation of Crystalline Polymorph J of Zoledronic Acid

Zoledronic acid (50gm) was refluxed with distilled water (750 mL) at 95-100° C. until it dissolved and followed by filtration to get the clear solution. This solution was then stirred at 5° C. The solid obtained was filtered and suck dried to get the crystalline polymorph J of zoledronic acid as final product (40.0 gm).

Example 2

Preparation of Risedronic Acid

Method—A

3-Pyridyl acetic acid (50 gm), phosphorous acid (105 gm) and n-octane (1000 mL) were taken in a four necked round bottom flask fitted with an addition funnel, mechanical stirrer, condenser and thermometer pocket and allowed to stir at 90-95° C. Phosphorus trichloride (175 gm) was then added to the reaction mixture and allowed to heat at 90-95° C. The reaction mixture was cooled and distilled water (500 mL) was added to it. The reaction mixture was further heated to 90-95° C. and then cooled. Methanol (1000 mL) was added to the reaction mixture and solution was further cooled to 0-5° C. and stirred for 4-5 hrs. The precipitated solid was filtered, washed with methanol and dried under vacuum yielding 99 gm of product.

Method—B

3-Pyridyl acetic acid (50 gm), phosphorous acid (105 gm) and 1,4dioxane (1000 mL) was taken in a four necked round bottom flask fitted with an addition funnel, mechanical stirrer, condenser and thermometer pocket and allowed to stir at 90-95° C. Phosphorus trichloride (175 gm) was then added to the reaction mixture and allowed to heat at 90-95° C. The reaction mixture was cooled and distilled water (500 mL) was added to it. The reaction mixture was further heated to 90-95° C. It was then cooled and methanol (5000 mL) was added to it. The solution was further cooled to 0-5° C. and stirred for 4-5 hrs. The precipitated solid was filtered, washed with methanol and dried under vacuum yielding 65 gm of product.

Amorphous Form of Risedronate Sodium

Risedronic acid (5 gm) was suspended in 87.5 ml of water. Sodium hydroxide (0.71 gm) was added and the solution became clear within 1 hour. The clear solution was then subjected to freeze-drying. White colored solid product was obtained after freeze-drying. XRD data confirmed it to be an amorphous form.

Amorphous Form of Risedronate Sodium from Crystalline Risedronate Sodium

Crystalline risedronate sodium (5 gm) was dissolved in 87.5 ml of water and stirred to get a clear solution. The clear solution was then subjected to freeze-drying. White colored solid product was obtained after freeze-drying. XRD data confirmed it to be an amorphous form.

Example 3

Preparation of Alendronic Acid

4-Aminobutyric acid (50 gm), phosphorous acid (140 gm) and n-octane (1000 mL) was taken in a four necked round bottom flask fitted with an addition funnel, mechanical stirrer, condenser and thermometer pocket and allowed to stir at 90-95° C. Phosphorus trichloride (240 gm) was then added to the reaction mixture and allowed to heat at 90-95° C. The reaction mixture was cooled and distilled water (500 mL) was added to it. The reaction mixture was further heated to 90-95° C. It was then cooled and ethanol (1000 mL) was added to it. The solution was further cooled to 0-5° C. and stirred for 4-5 hrs. The precipitated solid was filtered and washed with ethanol and dried under vacuum to yield 52.0 gm product.

Example 4

Preparation of Minodronic Acid

Imidazo[1,2-a]pyridin-3-yl acetic acid (46 gm), phosphorous acid (75 gm) and 1,4-Dioxane (900 mL) was taken in a four necked round bottom flask fitted with an addition funnel, mechanical stirrer, condenser and thermometer pocket and allowed to stir at 90-95° C. Phosphorus trichloride (130 gm) was then added to reaction mixture and allowed to heat at 90-95° C. The reaction mixture was cooled and distilled water (450 mL) was added to it. The reaction mixture was further heated to 90-95° C. It was then cooled and acetone (1400 mL) was added to it. The solution was further cooled to 0-5° C. and stirred for 4-5 hrs. The precipitated solid was filtered and dried under vacuum to give 44 gm of product.

Example 5

Preparation of Neridronic Acid

6-Aminobutyric acid (50 gm), phosphorous acid (110 gm) and 1,4-dioxane (1000 mL) was taken in a four necked round bottom flask fitted with an addition funnel, mechanical stirrer, condenser and thermometer pocket and allowed to stir at 90-95° C. Phosphorus trichloride (180 gm) was added in reaction mixture and allowed to heat at 90-95° C. The reaction mixture was cooled and distilled water (500 mL) was added to it. The reaction mixture was further heated to 90-95° C. It was then cooled and acetonitrile (1000 mL) was added to it. The solution was further cooled and stirred. The precipitated solid was filtered, washed with acetonitrile and dried in vacuum oven to give 49 gm of product.

Example 6

Preparation of Etidronic Acid

Acetic acid (50 g), phosphorous acid (240 gm) and 1,4-dioxane (1000 mL) was taken in a four necked round bottom flask fitted with an addition funnel, mechanical stirrer, condenser and thermometer pocket and allowed to stir at 90-95° C. Phosphorus trichloride (400 gm) was then added to the reaction mixture and allowed to heat at 90-95° C. The reaction mixture was cooled and distilled water (500 ml) was added to it. The reaction mixture was further heated to 90-95° C. It was then cooled and acetonitrile (1000 mL) was added to it. The solution was further cooled to 0-5° C. and stirred for 4-5 hrs. The precipitated solid was filtered, washed with acetonitrile and dried in vacuum oven to give 9 gm of product.

Certain modifications and improvements of the disclosed invention will occur to those skilled in the art without departing from the scope of invention, which is limited only by the appended claims.

We claim:

1. A process for producing bisphosphonic acids of formula (II) or their pharmaceutically acceptable salts, the process comprising reacting a carboxylic acid of Formula [I] with phosphorous acid and halophosphorus compound in the presence of a solvent selected from aliphatic hydrocarbons or water miscible cyclic ethers excluding dioxane at a temperature between about 60° C. to reflux temperature;

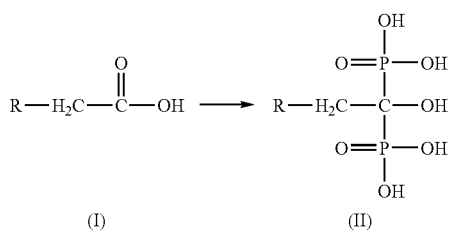

wherein, R is either imidazol-1-yl, 3-pyridyl, 2-aminoethyl, (N-(n-pentyl),N-methylamino) methyl, imidazo[1,2-a]pyridin-3-yl, 4-aminobutyl, (N,N-dimethylamino) methyl, hydrogen or aminomethyl.

2. The process according to claim 1 comprising the steps of:
   (a) reacting a carboxylic acid of Formula [I] with phosphorous acid and halophosphorus compound in the presence of a solvent selected from aliphatic hydrocarbons or water miscible cyclic ethers excluding dioxane at a temperature between about 60° C. to reflux temperature;
   (b) refluxing the resultant reaction mixture and cooling the same;
   (c) adding water to the same;
   (d) hydrolyzing the reaction mixture;
   (e) optionally adding anti-solvent to the reaction mixture; and
   (f) isolating the resultant bisphosphonic acid from the suspension.

3. The process according to claim 2, wherein said halophosphorus compound is selected from $PCl_3$, $PCl_5$, $POCl_3$, $PBr_3$, $PBr_5$ and $POBr_3$.

4. The process according to claim 2, wherein the carboxylic acid is selected from 4-aminobutanoic acid, (3-pyridyl)ethanoic acid, (imidazol-1-yl)ethanoic acid, 3-{N-(n-pentyl)-N-methylamino}propionic acid, (imidazo[1,2-a]pyridine-3-yl) ethanoic acid, 3-aminopropionic acid, 3-(N,N-dimethylamino)propionic acid, 6-aminohexanoic acid and ethanoic acid.

5. The process according to claim 2, wherein the resulting bisphosphonic acids comprise zoledronic acid, risedronic acid, alendronic acid, minodronic acid, neridronic acid, pamidronic acid, ibandronic acid, olpadronic acid or etidronic acid and their pharmaceutically acceptable salts.

6. The process according to claim 2, wherein the aliphatic hydrocarbon having $C_6$-$C_{10}$ atoms is selected from n-octane, iso-octane, cyclooctane, n-heptane, cycloheptane, n-hexane, cyclohexane or a mixture thereof.

7. The process according to claim 2, wherein the water miscible cyclic ether is tetrahydrofuran.

8. The process according to claim 2, wherein the anti-solvent is selected from lower alcohol, ketone, nitrile and cyclic ether.

9. The process according to claim 1 or 2, further comprising refluxing the bisphosphonic acid with distilled water at 95° C. to 100° C. until its dissolution followed by filtration to get clear solution, stirring the resultant solution at 5° C., filtering and drying the resultant to get crystalline polymorph, wherein the said bisphosphonic acid is zoledronic acid and said crystalline polymorphic form is Polymorph J of zoledronic acid.

10. The process according to claim 1 or 2, further comprising, treating the bisphosphonic acid with sodium base in water, removing water at low temperature and drying the resultant to obtain an amorphous form of sodium salt of bisphosphonic acid, wherein the said bisphosphonic acid is risedronic acid.

11. The process according to claim 10, wherein the sodium base is selected from the group consisting of sodium hydroxide, sodium carbonate, sodium bicarbonate and sodium alkoxide (wherein alkyl contains $C_1$-$C_6$ carbon atoms).

12. The process according to claim 1, further comprising, dissolving the sodium salt of a bisphosphonic acid in water, stiffing the same to make the solution clear, freezing the solution and removing the water by lyophilization and drying the resultant to obtain an amorphous form of sodium salt of said bisphosphonic acid, wherein the said bisphosphonic acid is risedronic acid.

* * * * *